United States Patent [19]

de Graaf et al.

[11] 4,386,207

[45] May 31, 1983

[54] PROCESS FOR THE PREPARATION OF C-SUBSTITUTED PYRIDINES AND/OR HYDROGENATED C-SUBSTITUTED PYRIDINES, QUINOLINES AND/OR HYDROGENATED QUINOLINES

[75] Inventors: Theodorus F. M. de Graaf, Beek; Charles H. Geersheuvels, Geleen, both of Netherlands

[73] Assignee: Stamicarbon B.V., Geleen, Netherlands

[21] Appl. No.: 321,055

[22] Filed: Nov. 13, 1981

[30] Foreign Application Priority Data

Nov. 15, 1980 [NL] Netherlands ................... 8006256

[51] Int. Cl.$^3$ ................ C07D 215/06; C07D 213/09
[52] U.S. Cl. ............................. 546/164; 546/166; 546/181; 546/184; 546/249; 546/251
[58] Field of Search ............ 546/164, 166, 181, 184, 546/249, 251

[56] References Cited

U.S. PATENT DOCUMENTS 4,276,419  6/1981  Verheijen et al. ............... 546/181

*Primary Examiner*—Henry R. Jiles
*Assistant Examiner*—Bernard Dentz

[57] ABSTRACT

An improved process for the preparation of pyridines and/or hydrogened pyridines that have been substituted with a hydrocarbon group at one or more carbon atoms. γ-cyanoketone, in a gaseous phase and in the presence of hydrogen, is passed over a first catalyst in a reaction zone to form a reaction mixture containing substituted pyridines and/or hydrogenated pyridines and hydrogen. A hydrogen-containing gas is separated from the reaction mixture and, prior to being recycled, is subjected to a two-step catalytic treatment. In the first catalytic treatment step, the hydrogen-containing gas is passed over an iron, nickel, cobalt, or platinum-containing catalyst at a temperature of between about 250° and 550° C. In the second catalytic treatment step, the hydrogen-containing gas is passed over an iron, nickel, or cobalt catalyst at a temperature of between about 550° and 800° C.

6 Claims, No Drawings

PROCESS FOR THE PREPARATION OF C-SUBSTITUTED PYRIDINES AND/OR HYDROGENATED C-SUBSTITUTED PYRIDINES, QUINOLINES AND/OR HYDROGENATED QUINOLINES

BACKGROUND OF THE INVENTION

This invention relates to a process for the preparation of pyridines and/or hydrogenated pyridines that have been substituted with a hydrocarbon group at one or more carbon atoms, by the gas phase catalytic cyclization of γ-cyanoketone in the presence of hydrogen.

It is known that these compounds can be prepared from a γ-cyanoketone by processes described in British Pat. Nos. 1,304,155 and 1,425,698. These processes are carried out, for instance, by passing the γ-cyanoketone, in a gas phase, and in the presence of hydrogen, over a catalyst containing a catalytically active metal or compound of metal selected from the group consisting of copper, silver, gold, iron, nickel, cobalt, ruthenium, rhodium, palladium, osmium, iridium and platinum. The resulting gaseous reaction mixture contains a fairly large quantity of hydrogen, which, after separation from the reaction mixture, can be recycled back to the reaction zone. However, it has been found that this separated hydrogen-containing gas, if directly recycled back to the reaction zone, causes the catalyst to lose activity and selectivity. In order to maintain the activity and selectivity of the catalyst used in the cyanoketone cyclization process at a high level, it has been suggested in U.S. Pat. No. 4,276,419 to first catalytically treat the hydrogen-containing gas by passing it over a catalyst containing iron, nickel, cobalt, or a compound of one of these metals, at a temperature of from about 300° to 800° C. before recycling it to the reaction zone.

It has now been found, however, that in such a catalytic treatment of the hydrogen-containing recycle gas, a carbon deposit will build up on the catalyst and the equipment used in the catalytic treatment in such a quantity that after a period of time, such as six days or so, the activity in the catalyst will be adversely affected, and the equipment will cease to function as required. The recycle of the hydrogen-containing gas must then be interrupted in order to replace the catalyst and clean the equipment, which can be quite costly.

SUMMARY OF THE INVENTION

It is an object of the present invention to provide an improvement to the process for preparing substituted pyridines and/or hydrogenated pyridines whereby hydrogen can be recovered and recycled without adversely affecting the activity and selectivity of the catalyst in the reaction zone. More specifically, it is an object of this invention to improve the catalytic treatment of the hydrogen-containing gas to be recycled so as to reduce the deposit of carbon on the catalyst and equipment used in the catalytic treatment.

It has now been found that in the catalytic treatment of the hydrogen-containing gas to be recycled, the deposit of carbon can be substantially avoided, or at least reduced to an acceptable minimum, by carrying out this catalytic treatment in two steps.

The improvement of this invention is particularly applicable to the preparation of pyridines and/or hydrogenated pyridines, which have been substituted with a hydrocarbon group on one or more carbon atoms, by the gas phase catalytic cyclization of a γ-cyanoketone in the presence of hydrogen, thereby forming a reaction mixture containing the reaction product and hydrogen. A hydrogen-containing gas is thereupon separated from the reaction mixture and recycled back to the reaction zone after being subjected to a catalytic treatment. The improvement of the present invention resides particularly in carrying out this catalytic treatment in two steps. In the first step, the hydrogen-containing gas to be recycled is passed over an iron, nickel, cobalt, or platinum-containing catalyst at a temperature of in the range of between about 250° and 550° C. In the second step, the hydrogen-containing gas from the first step is passed over an iron, nickel, or cobalt-containing catalyst at a temperature in the range of between about 550° and 800° C.

The iron, nickel, cobalt, or platinum-containing catalyst used in the improved catalytic treatment of this invention can be any of a number of known catalysts containing these materials. These catalysts may contain the metal as such, or as a compound of the metal such as an oxide, or as a mixture thereof. Also suitable for use in the first and/or second catalytic treatment steps are supported carriers wherein the catalytically active material is applied to a carrier, such as aluminum oxide, silicon oxide, magnesium oxide, or carbon. The use of a nickel catalyst has been found particularly suitable in both the first and second catalytic treatment steps.

The space velocity at which the gas is passed over the catalyst in the respective first and second catalytic treatment steps can be varied within wide limits, for instance from about 0.1 to 50 N-liters per gram of catalyst (including any carrier material to which it is applied) per hour. Preferably, however, in both the first and second catalytic treatment steps, the space velocity will be between about 0.25 and 20 N-liters of hydrogen-containing gas per gram of catalyst per hour.

In using the process of the present invention, it may be necessary to discharge a portion of the hydrogen-containing gas from the process in order to keep the concentration of impurities from building up to too high a level. In that case, it will be necessary to provide a fresh supply of hydrogen to the cyanoketone reaction zone to maintain the desired hydrogen/cyanoketone ratio. It has been found that a further advantage of the present invention is that impure hydrogen can be used (for instance hydrogen obtained as an off-gas in dehydrogenation-processes or in cracking of petroleum fractions) by introducing this impure hydrogen (containing e.g. carbonmonoxide and/or ammonia) into the hydrogen-containing gas to be recycled prior to subjecting it to the two-step catalytic treatment of this invention. In this manner, impure hydrogen can be used to maintain the desired hydrogen-cyanoketone ratio.

The temperature utilized in the first step catalytic treatment in accordance with the invention should be within the range of between about 250° and 550° C. and preferably will be in the range of between about 300° and 500° C. The temperature utilized in the second catalytic treatment step should be in the range of between about 550° and 800° C., however, preferably a temperature in the range of between about 575° and 700° C. will be used.

In applying the improved process of the present invention, as in applying the basic process known in the art, various γ-cyanoketones can be used as starting materials, such as 5-oxohexanenitrile, 5-oxoheptanenitrile, 4-methyl-5-oxohexanenitrile, 2-(β-cyanoethyl)- cyclohexanone, 4-phenyl-5-oxohexanenitrile, and 4-methyl-5-oxoheptanenitrile. The process according to the invention is particularly suitable for the preparation of 2-methyl-pyridine, 2,3-lutidine, and quinoline starting from, respectively, 5-oxohexanenitrile, 4-methyl-5-oxohexanenitrile, and 2-(β-cyanoethyl)-cyclohexanone.

The compounds obtained in applying the process according to the invention can be used for various purposes, for instance for the preparation of herbicides.

DETAILED DESCRIPTION OF PREFERRED EMBODIMENTS

The preferred embodiments of the improved process of the present invention will be illustrated by the following examples, and compared to a process wherein only a single catalytic treatment step is used.

EXAMPLES I-V

A gaseous mixture of 5-oxohexanenitrile and hydrogen was obtained by vaporizing liquid 5-oxohexanenitrile and mixing it with hydrogen and the recycled hydrogen-containing gas obtained in this process. This gaseous mixture was passed through a catalyst bed contained in a tubular reactor having a diameter of 25 mm and a length of 500 mm, which was provided with a heating jacket. The catalyst bed consisted of 50 grams of a palladium on aluminum oxide catalyst with 0.5 percent by weight Pd. The temperature of the catalyst bed was maintained at 240° C. The space velocity of the nitrile was 0.15 gram per gram of catalyst per hour, and the space velocity of the hydrogen was 0.15 N-liter hydrogen per gram of catalyst per hour.

The reaction mixture obtained was passed through an ice-cooled receiving tank in which the reaction product condensed. The remaining noncondensed gaseous reaction mixture, mainly consisting of hydrogen, was passed, at elevated temperature, through a second tubular reactor containing a bed of 7.5 grams of nickel catalyst (16.1% by weight of Ni in respect of SiO2, grade G1-G22 of BASF). The second tubular reactor had a diameter of 10 millimeters and a length of 250 millimeters, and the temperature of the catalyst bed in the second reactor was varied between 300° and 500° C. as shown on the table which follows. The space velocity in the second reactor was varied between 0.35 and 6 N-liters of hydrogen-containing gas per gram of nickel catalyst per hour, also as shown on the table below.

The gas mixture obtained from the second reactor was subsequently passed through a third tubular reactor having the same dimensions as the second tubular reactor, and filled with a catalyst bed consisting of 7.5 grams of the same nickel catalyst. The catalyst bed in the third reactor was maintained at a temperature of 650° C. The hydrogen-containing gas obtained from the third reactor was recirculated to the inlet of the first reactor in which the 5-oxohexanenitrile was converted. By discharging a portion of this gas, the concentration of hydrogen in the recirculated gas was kept above 99%. Fresh hydrogen, having a purity of 99.9%, was supplied to maintain the amount of hydrogen to be passed through at the desired value.

After operating for a period of ten days, the quantity of 5-oxohexanenitrile introduced into the process, and the quantity of reaction product obtained, were measured under constant conditions for one hour. The quantity of 5-oxohexanenitrile introduced into the process was determined by measuring the weight loss of the liquid 5-oxohexanenitrile.

The reaction product was analyzed by gas chromatography and the results are summarized on the following table in terms of the percent conversion of the amount of nitrile initially introduced into the process, and the selectivity of that conversion to 2-methylpyridine and 2-methylpiperidine as a percentage of nitrile converted.

The table additionally shows the results of comparative example A which reports the results of an experiment in which none of the hydrogen-containing gas was recycled to the first reactor.

| example | temperature nickel catalyst in 2nd reactor in °C. | space velocity 2nd reactor | conversion of nitrile in % | selectivity 2-methyl-pyridine in % | selectivity 2-methyl-piperidine in % |
|---|---|---|---|---|---|
| I | 400 | 2 | 99.9 | 83.8 | 4.6 |
| II | 350 | 1 | 100 | 84.1 | 4.5 |
| III | 300 | 0.35 | 99.9 | 83.7 | 4.6 |
| IV | 500 | 3 | 99.8 | 84.0 | 4.5 |
| V | 450 | 6 | 99.9 | 83.9 | 4.6 |
| A | — | — | 100 | 84.2 | 4.6 |

A comparative example B was also begun wherein the hydrogen-containing gas from the first reactor bypassed the second reactor and was introduced directly into the third reactor. This comparative example B had to be discontinued after six days because of clogging in the third reactor resulting from carbon deposits.

EXAMPLE VI

Example I and the comparative examples were repeated under the same conditions (except using a temperature of 230° C. in the first reactor) with 4-methyl-5-oxohexanenitrile instead of 5-oxohexanenitrile. The conversion of 4-methyl-5-oxohexanenitrile was 99.2%, and the selectivity to 2,3-dimethylpyridine was 89.1% and the selectivity to 2,3-dimethylpiperidine was 9.1%. With comparative example VI A (without recycle of the hydrogen-containing gas) these values were 99.6%, 89.6%, and 8.8% respectively. With comparative example VI B (in which the hydrogen-containing gas to be recycled was fed directly to the third reactor without treatment in the second reactor) these values were 97.2%, 84.7%, and 9.0% respectively. Moreover, with comparative example VI B, the pressure differential over the third reactor showed a strong increase, indicating that carbon deposits were building up.

EXAMPLE VII

In the same way as in Example I, 2-(β-cyanoethyl)cyclohexanone was passed over 50 grams of the same Pd catalyst, while the catalyst temperature was maintained at 210° C. The space velocity of the cyanoketone was 0.15 gram per gram of Pd catalyst per hour, and the space velocity of the hydrogen was 0.3 N-liter per gram of catalyst per hour. The hydrogen-containing gas to be recycled was passed through the second reactor at 450° C. and subsequently through the third reactor at 650° C. The space velocity of the gas passing through the second and third reactors was 1 N-liter per gram of catalyst per hour.

For the purpose of comparison, an experiment VII A was made without any recycle of hydrogen and, under the same conditions, another experiment VII B was made with recycle of hydrogen in which the hydrogen-containing gas mixture to be recycled was passed directly to the third reactor without treatment in the second reactor. For example VII, and comparative experiment VII A (without hydrogen recycle) the conversion of 2-(β-cyanoethyl)cyclohexanone was 99.8% and 100% respectively. In both cases the selectivity to quinoline was 1% and the selectivity to decahydroquinoline was 48%. The selectivity to 1,2,3,4-tetrahydroquinoline was 5% and 6% respectively, and the selectivity to 5,6,7,8-tetrahydroquinoline was 43% and 42% respectively. Comparative experiment VII B (with the recirculation of hydrogen only via the third reactor) had to be discontinued prematurely on account of clogging.

What is claimed is:

1. In a process for the preparation of pyridines and/or hydrogenated pyridines that have been substituted with a hydrocarbon group at one or more of the carbon atoms, by the steps of:

passing a γ-cyanoketone, in a gaseous phase in the presence of hydrogen, over a first catalyst containing a catalytically active component selected from the group consisting of copper, silver, gold, iron, nickel, cobalt, ruthenium, rhodium, palladium, osmium, iridium, platinum and compounds thereof, thereby forming a reaction mixture containing said substituted pyridines and/or hydrogenated pyridines and hydrogen;

separating a hydrogen-containing gas from said reaction mixture; and subjecting at least a portion of said hydrogen-containing gas to a catalytic treatment and thereafter recycling it to said reaction zone, the improvement comprising carrying out said catalytic treatment in at least two steps wherein, in said first step, said hydrogen-containing gas to be recycled is passed over a catalyst containing a component selected from the group consisting of iron, nickel, cobalt, platinum, and compounds thereof, at a temperature in the range of between about 250° and 550° C.; and in said second step, said hydrogen-containing gas to be recycled is passed over a catalyst containing a component selected from the group consisting of iron, nickel, cobalt, and compounds thereof, at a temperature of between about 550° to 800° C.

2. The process of claim 1 wherein the catalyst in both said first and second steps contains nickel.

3. The process of claim 1 or 2 wherein the space velocity of said hydrogen-containing gas in both said first and second steps is in the range of between about 0.25 and 20 N-liters of said gas per gram of catalyst per hour.

4. The process of claim 1 or 2 wherein only a portion of said hydrogen-containing gas separated from said reaction mixture is recycled to said reaction zone.

5. The process of claim 4 wherein additional hydrogen is introduced into said process by adding impure hydrogen to said hydrogen-containing gas to be recycled prior to subjecting said hydrogen-containing gas to said two-step catalytic treatment.

6. The process of claim 1 or 2 wherein said first step is carried out at a temperature of between about 300° and 500° C., and said second step is carried out at a temperature of between about 575° and 700° C.

* * * * *